(12) United States Patent
Futamura et al.

(10) Patent No.: US 8,007,105 B2
(45) Date of Patent: Aug. 30, 2011

(54) LENS FOR INTRAOCULAR OBSERVATION AND CONTACT LENS FOR VITREOUS SURGERY

(75) Inventors: Hideyuki Futamura, Tokyo (JP); Kazuaki Kadonosono, Yokohama (JP)

(73) Assignee: Hoya Corporation, Tokyo (JP)

( * ) Notice: Subject to any disclaimer, the term of this patent is extended or adjusted under 35 U.S.C. 154(b) by 177 days.

(21) Appl. No.: 11/663,837

(22) PCT Filed: Sep. 28, 2005

(86) PCT No.: PCT/JP2005/017802
§ 371 (c)(1),
(2), (4) Date: Aug. 2, 2007

(87) PCT Pub. No.: WO2006/038501
PCT Pub. Date: Apr. 13, 2006

(65) Prior Publication Data
US 2007/0268450 A1 Nov. 22, 2007

(30) Foreign Application Priority Data
Oct. 1, 2004 (JP) .................. 2004-290196

(51) Int. Cl.
*A61B 3/00* (2006.01)
*A61B 3/125* (2006.01)
(52) U.S. Cl. ........................................ 351/219; 351/205
(58) Field of Classification Search ............... 351/160 R, 351/160 H, 205, 206, 219
See application file for complete search history.

(56) References Cited

U.S. PATENT DOCUMENTS

| | | | | |
|---|---|---|---|---|
| 5,172,269 A | * | 12/1992 | Ogura et al. | 359/580 |
| 5,200,773 A | * | 4/1993 | Volk | 351/219 |
| 5,436,680 A | | 7/1995 | Volk | |
| 5,548,352 A | | 8/1996 | Dewey | |
| 6,621,634 B2 | * | 9/2003 | Hanaoka et al. | 359/582 |
| 7,354,151 B2 | * | 4/2008 | Eisenberg | 351/200 |
| 2004/0105248 A1 | * | 6/2004 | Yu et al. | 362/31 |
| 2005/0041298 A1 | | 2/2005 | Toda et al. | |

FOREIGN PATENT DOCUMENTS

| | | |
|---|---|---|
| DE | 36 07 860 A1 | 9/1987 |
| EP | 0 390 218 A2 | 10/1990 |
| EP | 0 928 977 A1 | 7/1999 |
| JP | U 58-81501 | 6/1983 |

(Continued)

OTHER PUBLICATIONS

Kadonosono et al., "Multicoated Contact Lens for Bimanual Vitreous Surgery Without Endoillumination," Arch Ophthalmol vol. 122, pp. 367-368, Mar. 2004.

(Continued)

*Primary Examiner* — Scott J Sugarman
(74) *Attorney, Agent, or Firm* — Oliff & Berridge, PLC

(57) ABSTRACT

An object of the present invention is to provide a contact lens for vitreous surgery that is highly durable to washing, disinfectants, sterilizing high-pressure steam, and the like, and that has good antireflection effect in the visible light range. In the contact lens 10 for vitreous surgery used to observe the ocular fundus 3 during vitreous surgery, an antireflection film 14 produced by ion beam sputtering is coated onto the upper surface 13 of a lens main body 11, and the antireflection film is a multilayered film in which a high refractive index layer 18 that contains tantalum pentoxide ($Ta_2O_5$) and a low refractive index layer 19 that contains silicon dioxide ($SiO_2$) are alternatingly layered.

6 Claims, 8 Drawing Sheets

| | FOREIGN PATENT DOCUMENTS | | |
|---|---|---|---|
| JP | 04204902 A | * | 7/1992 |
| JP | A 7-234302 | | 9/1995 |
| JP | A 2001-183609 | | 7/2001 |
| JP | A-2001-346763 | | 12/2001 |
| JP | A 2004-170500 | | 6/2004 |
| WO | WO 00/36456 A1 | | 6/2000 |
| WO | WO 2004/046769 A1 | | 6/2004 |

OTHER PUBLICATIONS

Nov. 4, 2010 Office Action issued in European Patent Application No. 05788171.6.

* cited by examiner (A)

(B)

LENS FOR INTRAOCULAR OBSERVATION AND CONTACT LENS FOR VITREOUS SURGERY

TECHNICAL FIELD

The present invention relates to a lens for intraocular observation held on the cornea and used for observing inside the eye, and to a contact lens for vitreous surgery held on the cornea during vitreous surgery and used for observing the ocular fundus.

BACKGROUND ART

Vitreous surgeries performed on the eye of a patient suffering from diabetic retinopathy, macular pigment degeneration, or vitreous hemorrhage, which are leading causes of loss of sight, are performed by mounting a contact lens for vitreous surgery of the cornea by way of an ophthalmic viscoelastic substance in order to clearly observe the interior of the eye under a operation microscope. The surgeon holds in his dexterous hand a vitreous cutter, vertical scissors, or other intraocular operative instrument, and holds in his non-dexterous hand an intraocular illumination guide connected to a light source apparatus via an optical fiber. In this manner, since only one hand can be used in the intraocular operation (hereinafter referred to as "one-hand method"), skill is required and the operation requires a considerable length of time.

For example, in the procedure for detaching the inner limiting membrane of the topmost layer of the retina, or detaching a proliferative membrane, which is one cause of retinal detachment, from the retina, the surgeon must maintain a very high level of concentration over a long period of time. When the procedure is performed from the peripheral portion of the ocular fundus inside the eye to the most peripheral portion of the ocular fundus, the iris becomes an obstacle and the area to be treated can not be viewed from the pupil. Therefore, a surgeon's assistant must press the area to be treated from the exterior of the eyeball toward the interior of the eyeball, and when pressure cannot be applied in the manner that surgeon desires, the surgeon and assistant both experience stress.

A method is being studied that allows the surgeon to perform intraocular procedures using both hands (hereinafter referred to as the "two-hand method"), whereby an illumination apparatus (extraocular illumination) mounted on a surgical microscope is used in lieu of a fiber illumination source that is inserted into the eye in order to illuminate the inside of the eye via the cornea and the contact lens for vitreous surgery. However, a portion of the illumination light reflects from the surface of the lens, the surgeon experiences glare, and the quality of the ocular fundus image is reduced by the reflected light.

The quantity of light directed into the eye by the extraocular illumination source described above is low in comparison with the quantity of intraocular illumination. Therefore, a more distinct ocular fundus image must be obtained by reducing the reflective loss on the surface of the lens and increasing, even by a small amount, the light rays transmitted through the contact lens for vitreous surgery.

An antireflection film disposed on the contact lens for vitreous surgery preferably has an antireflective effect that extends over a range that is as wide as possible in the visible light region of 400 nm to 780 nm in order to obtain a naturally colored observation image.

Initially, the inventors provided an antireflective coating using vacuum deposition, which is widely used for intraocular lens and the like, in order to first coat an antireflective film on a contact lens for vitreous surgery. The reflection of illumination light is reduced, but the vacuum-deposited film is not highly durable to washing, disinfectants, and sterilizing high-pressure steam, and repeated use as a surgical lens was not possible.

Contact lenses for vitreous surgery and lenses for intraocular observation have lengthy contact with water, corrosive medicines, and sterilizing high-pressure steam; the contact surface area is considerable; and the temperature at the time of contact is high in comparison with environments in which lens used in spectacles, cameras, binoculars, microscopes, and other optical instruments are employed. In other words, an antireflective film coated onto a contact lens for vitreous surgery and a lens for intraocular observation have a much greater need for high durability in comparison with the durability required in an antireflective film for the optical equipment described above.

With conventionally used vacuum deposition and ordinary sputtering, it is difficult to obtain durability performance required in a lens for intraocular observation and a contact lens for vitreous surgery, even if the film formation substance and film composition are changed. For example, Patent Document 1 proposes a moisture proof antireflection film that has a high refractive index layer composed of $HfO_2$ and $Ta_2O_5$, and a low refractive index layer composed of $SiO_2$.

[Patent Document 1] Japanese Laid-open Patent Application No. 7-234302

DISCLOSURE OF THE INVENTION

Problems that the Invention is to Solve

However, the antireflection film is a layer composed of a high refractive index material, which is opposite from the normal film design of an outermost layer on the atmosphere side. Impurities easily contaminate the antireflection film, and a tough, dense film is difficult to form. Therefore, a high level of durability required in a lens for intraocular observation and a contact lens for vitreous surgery cannot be achieved, and at the same time, an antireflective effect across the visible light region of 400 nm to 700 nm cannot be obtained.

In view of the foregoing, an object of the present invention is to provide a lens for intraocular observation and a contact lens for vitreous surgery that are highly durable to washing, disinfectants, sterilizing high-pressure steam, and the like, and that have good antireflection effect in the visible light range.

A first aspect of the present invention is a lens for intraocular observation that is held on a cornea and is used for observing inside the eye, wherein an antireflection film that is durable to high-pressure steam for sterilization is coated on at least a portion of the lens.

A second aspect of the present invention is a lens for intraocular observation that is held on a cornea and is used for observing inside the eye, wherein an antireflection film is coated on at least a portion of the lens via an ion beam sputtering method.

A third aspect of the present invention is the lens for intraocular observation of the first or second aspects, wherein the antireflective film is coated on the upper surface of the lens optical surface.

A fourth aspect of the present invention is the lens for intraocular observation of any of the first to third aspects, wherein the antireflective film is composed of a single layer or several layers.

A fifth aspect of the present invention is the lens for intraocular observation of any of the first to fourth aspects, wherein the antireflective film is a multilayered film in which a layer that contains silicon dioxide and a layer that contains tantalum pentoxide are alternatingly layered.

A sixth aspect of the present invention is the lens for intraocular observation of the fifth aspect, wherein the topmost layer of the antireflective film is a layer that contains silicon dioxide.

A seventh aspect of the present invention is the lens for intraocular observation of any of the first to sixth aspects, wherein the target used in the ion sputtering method is a metal oxide.

An eighth aspect of the present invention is the lens for intraocular observation of any of the first to seventh aspects, wherein the lens material is glass or transparent plastic.

A ninth aspect of the present invention is a contact lens for vitreous surgery used to observe an ocular fundus during vitreous surgery, wherein the lens for intraocular observation of any of the first to eighth aspects is used.

Effect of the Invention

In accordance with the first, second, fourth, fifth, seventh, eighth, and ninth aspects, an antireflection film is coated onto at least a portion of a lens for intraocular observation and a contact lens for vitreous surgery, thereby achieving a good antireflective effect in the visible light region. Therefore, reflection on the lens surface is reduced and, in the case of a lens for intraocular observation, an observer can clearly observe the interior of the eye without being affected by reflected light. Also, in the case of a contact lens for vitreous surgery, the surgeon can clearly observe the ocular fundus image without the annoyance of strong reflected light from extraocular illumination. For this reason, there is no longer a need to provide intraocular illumination during vitreous surgery, and the intraocular procedure (two-hand method) can be performed using both hands.

The antireflection film is formed by ion beam sputtering. Therefore, impurities do not easily enter into the antireflection film, and a tough, dense film can be obtained. As a result, an antireflection film that is highly durable to washing, disinfectants, sterilizing high-pressure steam, and the like can be obtained.

In accordance with the third to ninth aspects, an antireflection film is coated on the upper surface of the optical surface of the lens, and an antireflective effect can therefore be made more efficient by coating an antireflection film in highly reflective locations (upper surface) on a lens for intraocular observation or a contact lens for vitreous surgery.

In accordance with the sixth to ninth aspects, the topmost layer of the antireflection film is a layer that contains silicon dioxide, and silicon dioxide is a component of quartz glass, which is a material that has a record of use in lenses for intraocular observation and contact lenses for vitreous surgery. Therefore, the safety of the lens for intraocular observation or contact lens for vitreous surgery can be sufficiently assured.

BEST MODE FOR CARRYING OUT THE INVENTION

Preferred embodiments for implementing the present invention are described below with reference to the diagrams.

FIG. 1 is a cross-sectional diagram showing the state in which an embodiment of the contact lens for vitreous surgery according to the present invention is held on the cornea of an eyeball. FIG. 2 is a cross-sectional diagram showing the structure of the antireflection film on the contact lens for vitreous surgery of FIG. 1.

Since vitreous surgery of the eyeball 1 is performed while observing the vitreous 2 or the ocular fundus 3, a contact lens 10 for vitreous surgery is held on the cornea 4, and the vitreous 2 or ocular fundus 3 is observed through a surgical microscope 9 and the contact lens 10 for vitreous surgery. The main body 11 of the contact lens 10 for vitreous surgery is composed of a lower surface 12 provided with a curved surface that matches the curvature of the cornea 4, and an upper surface 13 of the sloped surface that forms a prism lens. At least a portion of the optical surface of the lens main body 11 has an antireflection film 14 coated onto the upper surface 13 in the present embodiment, thus constituting the contact lens 10 for vitreous surgery. Reference numeral 5 in FIG. 1 is a crystalline lens.

The lens main body 11 is configured so that the contact lens 10 for vitreous surgery is placed on the cornea 4 by way of an ophthalmic viscoelastic substance (hyaluronic acid or the like), and the curvature of the lower surface 12 must therefore follow the curvature of the cornea 4. Since the radius of curvature of an adult cornea is ordinarily about 8 mm, the radius of the concave curvature of the lower surface 12 of the lens main body 11 is preferably about 8 mm. However, the radius is reduced for children.

In a prism lens, for example, the higher the refractive index of the lens material is, the more marked the effect of refracting the light is. The refractive index of the material of the lens main body 11 must be 1.35 or higher, and preferably 1.45 or higher in order to better observe the peripheral area of the ocular fundus. On the other hand, since reflected light increases as the refractive index of the lens material increases, an antireflection film can be used. Examples of the material of the lens main body 11 include optical glass and other glass, and transparent plastic or transparent elastomer.

Examples of optical glass include heavy lanthanum flint glass, lanthanum flint glass, heavy flint glass, lanthanum crown glass, heavy barium flint glass, barium flint glass, titanium flint glass, flint glass, light flint glass and other flint glasses, lanthanum crown glass, heavy crown glass, heavy lanthanum phosphate glass, light barium flint glass, barium crown glass, crown flint glass, crown glass, borosilicate crown glass, phosphate crown glass, fluorophosphate crown glass or another crown glass, and quartz glass, sapphire, ruby, and the like. Examples of transparent plastic include polyalkyl (meth)acrylates typified by polymethyl(meth)acrylate and copolymers thereof, as well as polystyrene, polycarbonate, styrene-acrylonitrile, CR-39, transparent, silicone and other transparent bodies. As long as the material is highly transparent, has a very low amount of striations or the like, and has excellent homogeneity, the material of the lens main body 11 is not limited to the materials listed above.

The lens main body 11, which forms a prism lens, is configured so that the upper surface 13 is sloped at a prescribed angle to the tangential plane of the lower surface 12, and this slope angle is the prism angle. The prism angle is determined by the desired observation site, and when the site is in the range between the intermediate peripheral portion of the ocular fundus and the peripheral portion of the ocular fundus, the suitable range is 5 to 70 degrees, and preferably 10 to 60 degrees. When the prism angle is less than 5 degrees, the effect of the prism cannot be sufficiently obtained. If the prism angle exceeds 70 degrees, the effective optical portion of the lens becomes narrow and distortions in the observed image become marked.

In a vitreous surgery, the pupil is dilated using a dose of a mydriatic agent, and the ocular fundus is viewed from the dilated pupil. The mydriatic diameter reaches a maximum of about 9 mm. Therefore, the outside diameter of the lens main body 11 must be greater than the mydriatic diameter, and about 10 to 14 mm is preferred.

The design of the antireflection film 14 coated onto the upper surface 13 of the lens main body 11 described above must account for the fact that the ocular fundus tissue must be brightly observable in natural colors. Therefore, a high level of light transmittance must be maintained over essentially the entire region of the visible light region, and reflectivity must be reduced. The sensitivity of the human eye with respect to light having different wavelengths is referred to as the "relative luminosity factor," and the factor shifts when the surrounding area is bright and when it is dark. The sensitivity of the human eye is acute with respect to light having a wavelength of 450 nm to 650 nm centered about the vicinity of 550 nm. Therefore, a contact lens for vitreous surgery, which requires observation of a more distinct ocular fundus image and low reflectivity performance on the lens surface produced by extraocular illumination (e.g., slit light used by a surgical microscope 9), is designed to have low reflectivity and a high level of light transmittance across substantially the entire region of visible light, i.e., 400 nm to 700 nm. Also, the antireflection film 14 requires durability in relation to washing, disinfectants, sterilizing high-pressure steam, and the like.

For this reason, the antireflection film 14 coated onto the upper surface 13 of the lens main body 11 is formed by ion beam sputtering. Ion beam sputtering directs an ion beam from an ion gun 16 onto a target 17 composed of metal or a metal oxide, as shown in FIG. 3. The particles of the sputtered target 17 collide with, and are deposited onto, the upper surface 13 of the lens main body 11 mounted on a holder 20, and the antireflection film 14 is coated onto the upper surface 13. The film produced by ion beam sputtering has little impurity contamination in comparison with a film produced by vacuum deposition, the film is tough and dense, and, as a result, the film is highly durable to washing, disinfectants, sterilizing high-pressure steam, and the like.

Examples of the substance constituting the target 17 include Al, Cr, Ag, TiN, ITO, $SiO_2$, $Al_2O_3$, $MgF_2$, TiO, Pt, $Ta_2O_5$, Ti, Au, Ni—Fe, $Si_3N_4$, Mo, and Ag alloys; Pyrex (registered trademark); and Nb, Si, and Al—Si. In particular, films for which $Ta_2O_5$ (tantalum pentoxide) and $SiO_2$ (silicon dioxide) are used as the target can satisfy the level of durability required in a contact lens for vitreous surgery.

In view of the above, the antireflection film 14 in the present embodiment is composed of a multilayered-film structure in which a plurality of high refractive index layers 18 composed of tantalum oxide ($Ta_2O_5$) and low refractive index layers 19 composed of silicon dioxide ($SiO_2$) are layered in an alternating fashion by ion beam sputtering. The topmost layer on the atmosphere side is composed of the low refractive index layer 19. The antireflection film 14 is not limited to the above-mentioned multilayered film, and the film may be a single-layer. In this case, the material of the single layer is preferably magnesium fluoride ($MgF_2$). Also, the antireflection film 14 may be composed by layering three or more materials having different indexes of refraction.

In view of the foregoing configuration, the following effects (1) to (4) are achieved in accordance with the embodiments described above.

(1) An antireflection film 14 is coated onto the upper surface 13 of the contact lens 10 for vitreous surgery, and reflection on the lens surface is therefore reduced because a good antireflective effect is obtained in the visible light region. The surgeon can distinctly observe the ocular fundus image without the annoyance of strong reflected light from the slit light of a surgical microscope 9 or other extraocular illumination source. For this reason, there is no longer a need for the surgeon to hold an intraocular illumination source with one hand during vitreous surgery, the intraocular procedure (two-hand method) can therefore be performed using both hands, and the operation can be performed with a low level of stress.

(2) The antireflection film 14 of the contact lens 10 for vitreous surgery is formed by ion beam sputtering. Therefore, impurities do not easily enter into the antireflection film 14, and a tough, dense film can be obtained. As a result, an antireflection film 14 that is highly durable to washing, disinfectants, sterilizing high-pressure steam, and the like can be obtained.

(3) An antireflection film 14 of the contact lens 10 for vitreous surgery is coated onto the upper surface 13 of the optical surface of the lens. Therefore, the antireflective effect can be made more efficient by coating an antireflection film 14 onto the upper surface 13 of the lens main body 11, which is highly reflective.

(4) The topmost layer of the antireflection film 14 of the contact lens 10 for vitreous surgery is a low refractive index layer 19 composed of silicon dioxide, and silicon dioxide is a component of quartz glass, which is a material that has a record of use in lenses for intraocular observation and contact lenses for vitreous surgery. Therefore, the safety of the contact lens 10 for vitreous surgery can be sufficiently assured.

EXAMPLES

The following examples describe the present invention in detail. Naturally, the present invention is not limited by the examples below.

Example 1

An antireflection film was formed on a flat quartz glass plate by ion beam sputtering. The film was composed of ten layers having a total thickness of 510 nm, wherein the first layer composed of $Ta_2O_5$ was formed to a thickness of 13 nm beginning from the flat plate surface, the second layer composed of $SiO_2$ was formed to a thickness of 38 nm, the third layer composed of $Ta_2O_5$ was formed to a thickness of 123 nm, the fourth layer composed of $SiO_2$ was formed to a thickness of 49 nm, the fifth layer composed of $Ta_2O_5$ was formed to a thickness of 9 nm, the sixth layer composed of $SiO_2$ was formed to a thickness of 91 nm, the seventh layer composed of $Ta_2O_5$ was formed to a thickness of 30 nm, the eighth layer composed of $SiO_2$ was formed to a thickness of 13 nm, the ninth layer composed of $Ta_2O_5$ was formed to a thickness of 63 nm, and the tenth layer composed of $SiO_2$ was formed to a thickness of 81 nm.

FIG. 4 shows the spectral reflection characteristics of the uncoated surface of a quartz glass plate and the antireflection film-coated surface when the antireflection film has not been coated on the quartz glass plate and when the film has been coated on the quartz glass plate. In FIG. 4, the reference letter A shows the spectral reflection characteristics of the coated surface, and the reference letter B shows the spectral reflection characteristics of the uncoated surface. FIG. 5 shows the light transmittance when the antireflection film has been coated on the quartz glass plate and when the film has not been coated on the quartz glass plate. In FIG. 5, the reference letter C shows the light transmittance when an antireflection film has been coated onto the quartz glass plate, and the reference letter D shows light transmittance when an antireflection film has not been coated onto the quartz glass plate.

With the quartz glass plate on which an antireflection film has been coated, the reflectivity was 0.7% or less and the transmissivity was about 96% across essentially the entire region of the visible light region of 400 nm to 700 nm required for observing the ocular fundus through the contact lens for vitreous surgery.

The following durability tests were subsequently performed on the contact lens for vitreous surgery on which the antireflection film had been coated on the upper surface of the quartz glass lens main body, and on the quartz glass plate on which the same antireflection film had been coated on the upper surface in the same manner. After each test was completed, the coated surface of the antireflection film was illuminated using strong white light, and the presence of degradation in the antireflection film was observed from the intensity of the reflected light and the color tone of the reflected image.

Water durability test: When a contact lens for vitreous surgery is used in actual practice, contact with body fluid and wash water is unavoidable. In view of this fact, [samples] were immersed in hot water at 55° C. for 24 hours, and the degradation of the antireflection film was evaluated.

Rub-washing durability test: Assuming that rub-washing will be used to remove unwanted matter deposited on the contact lens for vitreous surgery, the coated surface of the antireflection film was strongly rubbed 250 times on a kitchen sponge that had been lathered using a neutral detergent diluted in water. The degradation of the antireflection film was then evaluated.

Chemical resistance test: The contact lens for vitreous surgery and quartz glass plate were immersed in disinfectant ethanol at 55° C. for 24 hours to check the durability to ethanol for disinfection used in a wiping contact lens for vitreous surgery. The degradation of the antireflection film was then evaluated.

Disinfectant chemical resistance test: The contact lens for vitreous surgery and quartz glass plate were immersed for 72 hours in a glutaral disinfectant (product name: Cidexplus 28, 3.5%), which is a high level disinfectant that can destroy all microorganisms excluding spores. The degradation of the antireflection film was then evaluated.

EOG sterilization resistance test: A contact lens for vitreous surgery and a quartz glass plate were subjected to 50 sterilization cycles, a single cycle being 12 hours of exposure to ethylene oxide gas (EOG) at a temperature of 50° C. and a concentration of 20%. The degradation of the antireflection film was then evaluated.

High-pressure steam sterilization resistance test: A contact lens for vitreous surgery and a quartz glass plate were sterilized for 4 hours at 132° C. using a high-pressure steam sterilizer. The degradation of the antireflection film was then evaluated.

No differences were observed in the intensity of the reflected light and the color tone of the reflected image before and after the durability tests described above. No differences were observed in the reflectivity of the coated surface of the quartz glass plate on which the antireflection film had been coated before and after the durability tests (the high-pressure steam sterilization resistance test), as shown in FIG. 6. In FIG. 6, the reference letter X shows the reflectivity prior to the durability test, and the reference letter Y shows the reflectivity following the durability test.

Example 2

An antireflection film was formed on a flat quartz glass plate by ion beam sputtering. The film was composed of 12 layers having a total thickness of 511 nm, wherein the first layer composed of $Ta_2O_5$ was formed to a thickness of 13 nm beginning from the flat plate surface, the second layer composed of $SiO_2$ was formed to a thickness of 40 nm, the third layer composed of $Ta_2O_5$ was formed to a thickness of 42 nm, the fourth layer composed of $SiO_2$ was formed to a thickness of 4 nm, the fifth layer composed of $Ta_2O_5$ was formed to a thickness of 73 nm, the sixth layer composed of $SiO_2$ was formed to a thickness of 38 nm, the seventh layer composed of $Ta_2O_5$ was formed to a thickness of 12 nm, the eighth layer composed of $SiO_2$ was formed to a thickness of 102 nm, the ninth layer composed of $Ta_2O_5$ was formed to a thickness of 30 nm, the tenth layer composed of $SiO_2$ was formed to a thickness of 12 nm, the eleventh layer composed of $Ta_2O_5$ was formed to a thickness of 65 nm, and the twelfth layer composed of $SiO_2$ was formed to a thickness of 80 nm.

In the second example, results similar to those of the first example were obtained in relation to the spectral reflection characteristics and light transmittance described above. Results similar to those of the first example were also obtained in relation the intensity of the reflected light and the color tone of the reflected image before and after the durability tests. Results similar to those of the first example were also obtained in relation the reflectivity of the coated surface of the quartz glass plate before and after the durability tests.

Comparative Example 1

A three-layered coating composed of $Al_2O_3$, $ZrO_2$, and $MgF_2$, which is a standard antireflection multilayered film, was deposited on a quartz glass plate by vacuum deposition. The thickness of each of the layers was 125 nm, 250 nm, and 125 nm.

Immediately after the film was formed, the reflected white light illuminated on the coated surface of the antireflection film was a purplish-red color, the reflection was considerably reduced, and the film was confirmed to have excellent antireflective performance (FIG. 7A). However, when the plate was immersed for 20 minutes in hot water at 55° C. and the same antireflection film was then illuminated with white light, a portion 21 (see FIG. 7B) of the antireflection film had peeled and fallen away. Therefore, the reflection of the coated surface of the antireflection film had increased and degradation of the antireflection film was observed.

Comparative Example 2

A three-layered coating composed of $Al_2O_3$, $ZrO_2$, and $SiO_2$ was deposited on a quartz glass plate by vacuum deposition, and an antireflection multilayered film was formed. The thickness of each of the layers was 127 nm, 250 nm, and 127 nm.

Immediately after the film was formed, reflected white light illuminated on the coated surface of the antireflection film was a blue color, the reflection was considerably reduced, and the film was confirmed to have excellent antireflective performance (FIG. 8A). However, when the plate was treated for 30 minutes in a high-pressure steam sterilizer at 132° C., and the same antireflection multilayered film was then observed, nonuniformities in the reflected light were generated in a portion 22 (see FIG. 8B) of the coating, and degradation of the antireflection film was observed.

The present invention was described based on the above-described embodiments, but the present invention is not limited to these embodiments.

With the contact lens 10 for vitreous surgery described above, for example, the antireflection film 14 was coated only on the upper surface 13 of the lens main body 11, but the antireflection film 14 may be coated onto the lower surface 12 of the lens main body 11 and/or the lateral peripheral surfaces 15 of the lens main body 11.

In the embodiments and examples, the case of a contact lens 10 for vitreous surgery was described. However, the present invention may also be applied to a lens for intraocular observation held on the cornea and used for observing the interior of the eye, may be used as a surgical lens in common ophthalmic surgery, and may also be used in examinations and diagnoses as well as surgery. In this case, good antireflection effect in the visible light range can be achieved because an antireflection film 14 is coated onto at least a portion (e.g., upper surface 13) of the lens main body 11. Therefore, reflection is reduced on the lens surface and an observer can distinctly observe the interior of the eye without being affected by reflected light.

KEY

Figure 1:
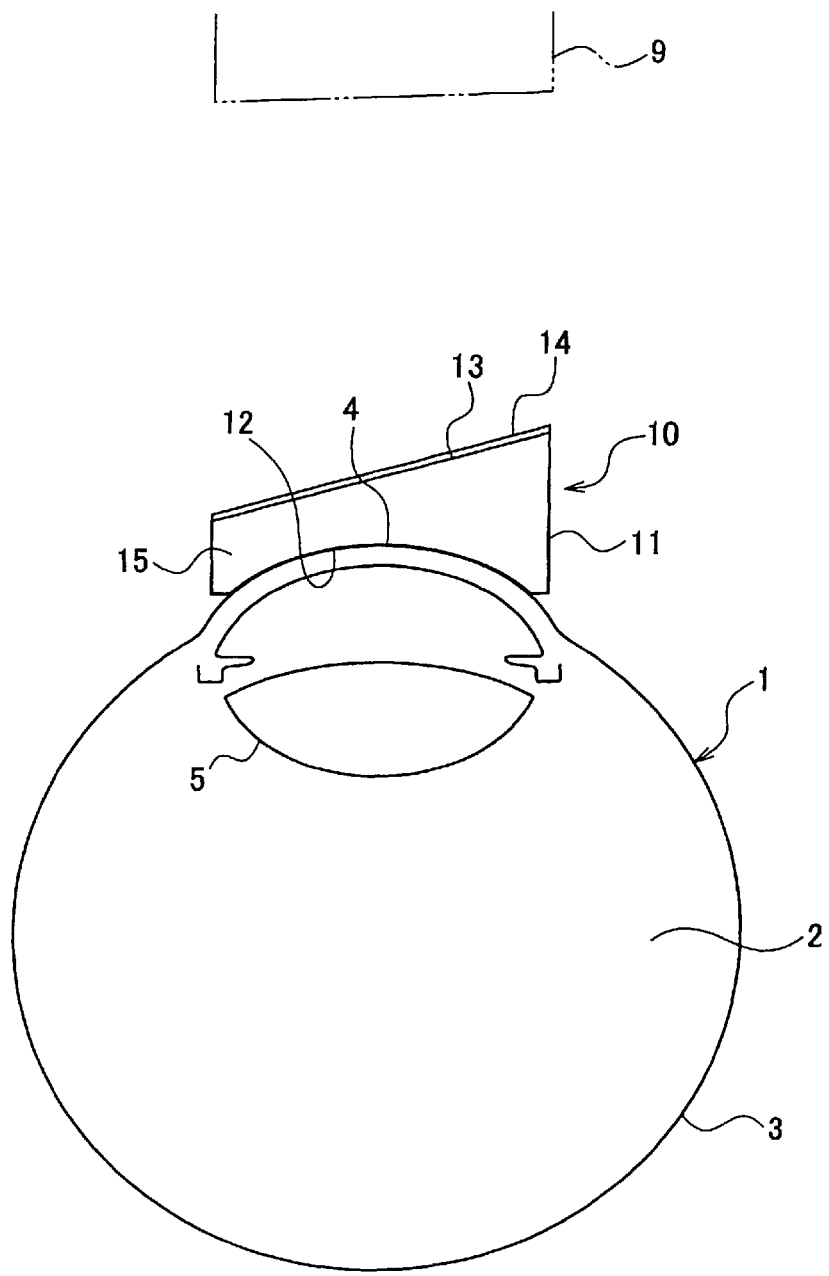
FIG. 1 is a cross-sectional diagram showing the state in which an embodiment of the contact lens for vitreous surgery according to the present invention is held on the cornea of an eyeball.
Figure 2:
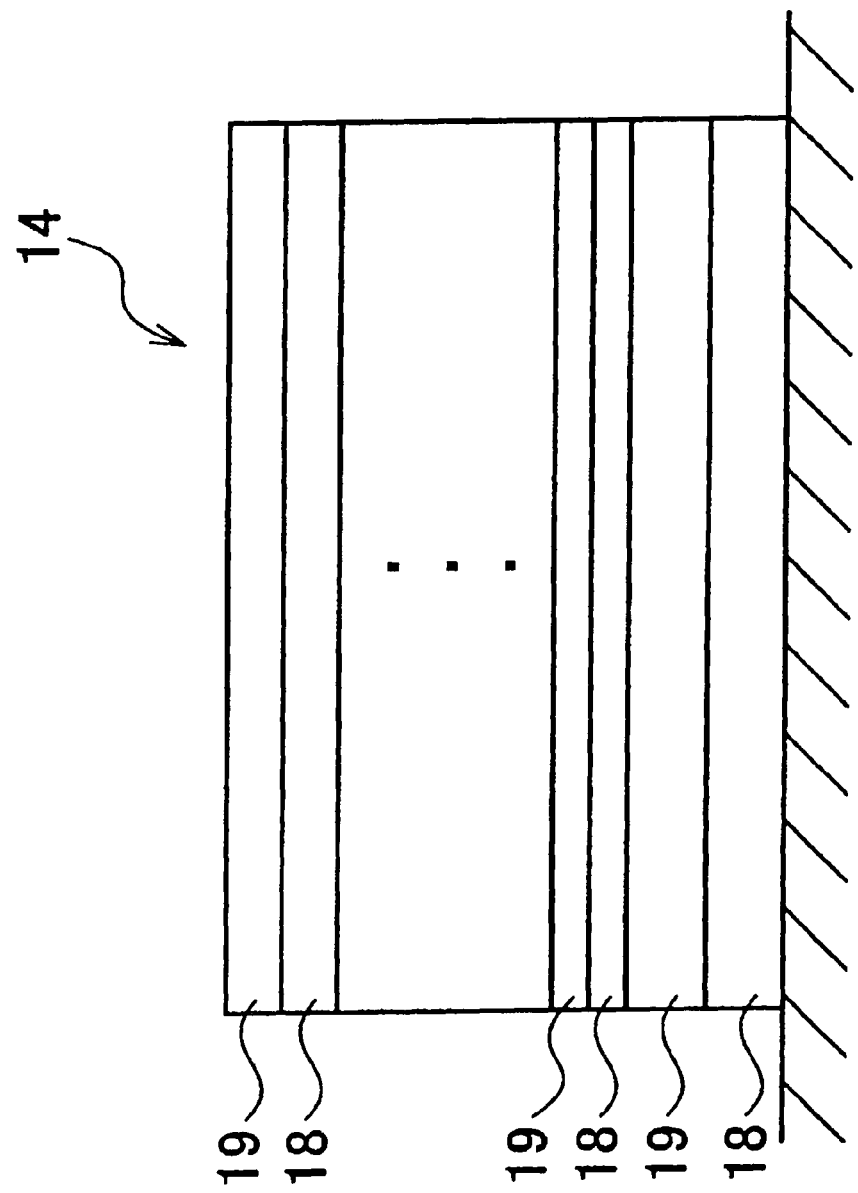
FIG. 2 is a cross-sectional diagram showing the structure of the antireflection film on the contact lens for vitreous surgery of FIG. 1.
Figure 3:
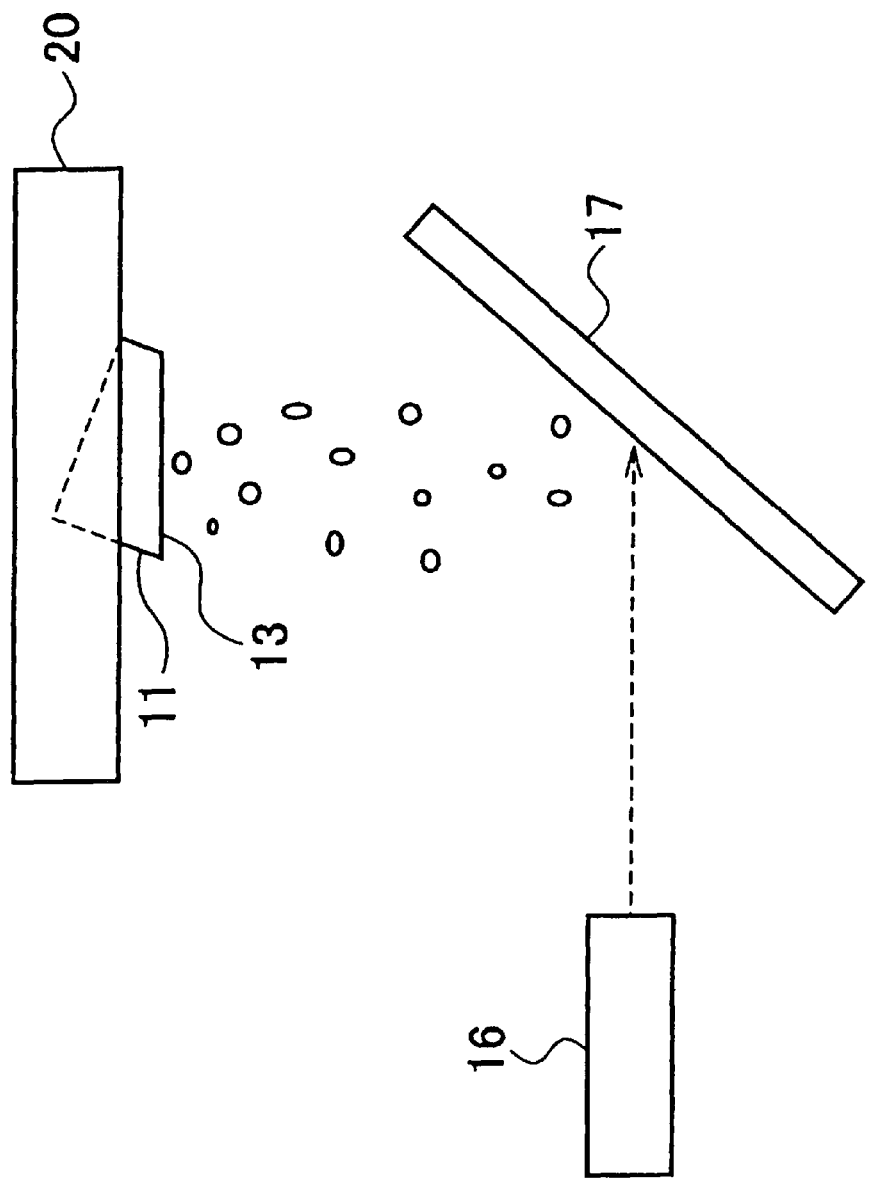
FIG. 3 is a schematic side view showing the configuration of the ion beam sputtering apparatus used for coating the antireflection film of FIG. 2.
Figure 4:
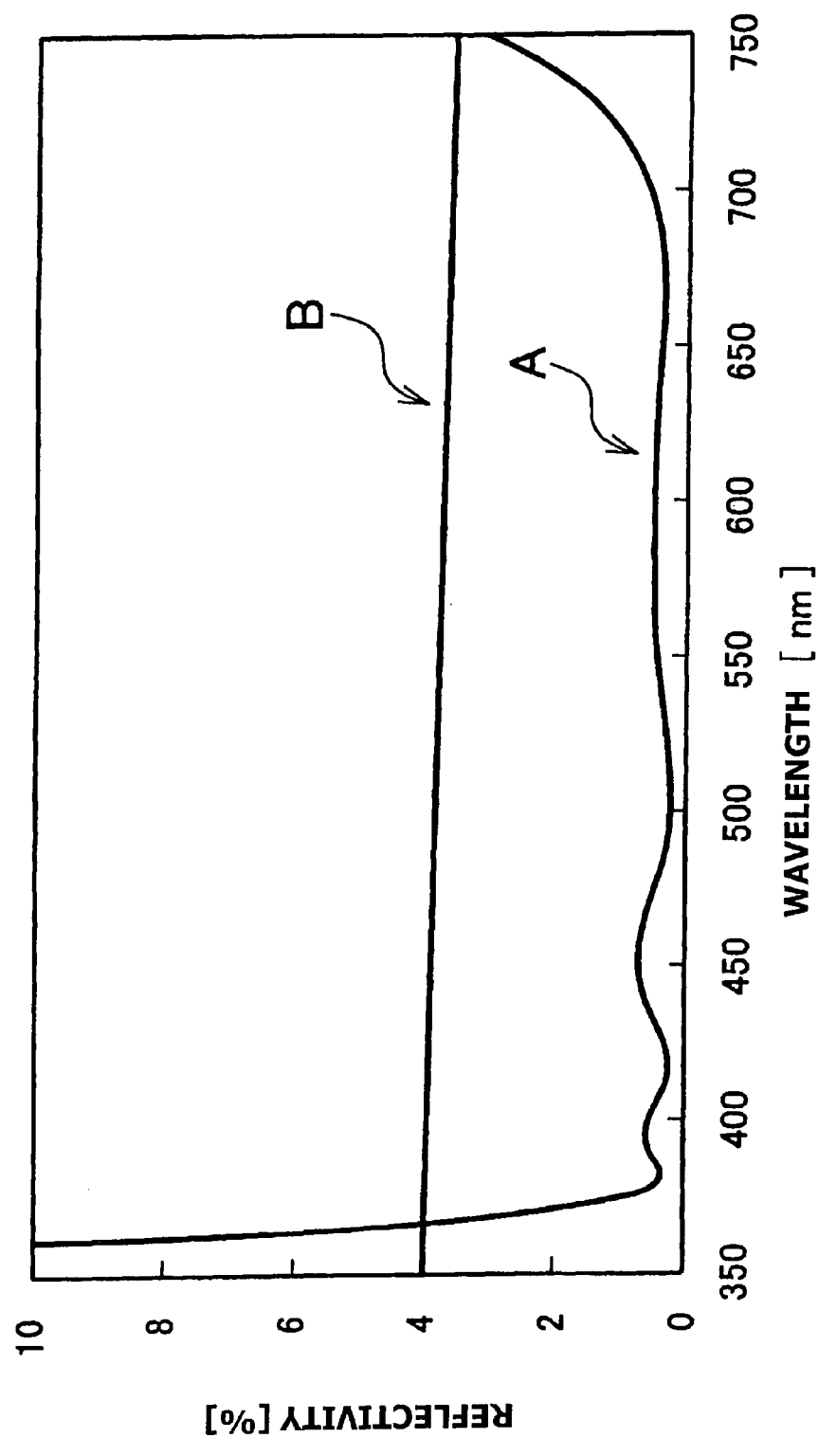
FIG. 4 is a graph showing the spectral reflection characteristics when the antireflection film of FIG. 2 has been coated on the quartz glass plate and when the film has not been coated on the quartz glass plate.
Figure 5:
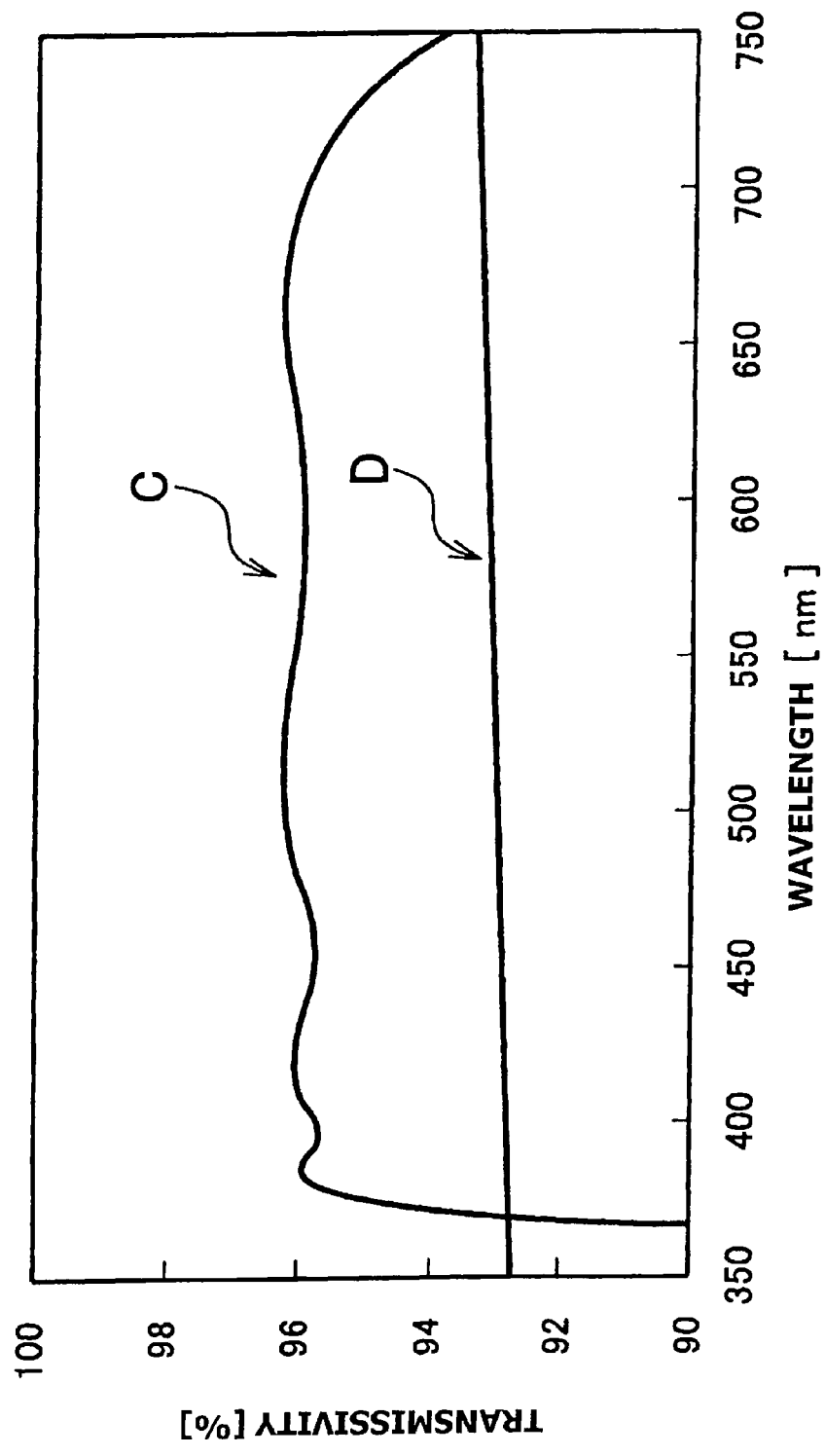
FIG. 5 is a graph showing the light transmittance when the antireflection film of FIG. 2 has been coated on the quartz glass plate and when the film has not been coated on the quartz glass plate.
Figure 6:
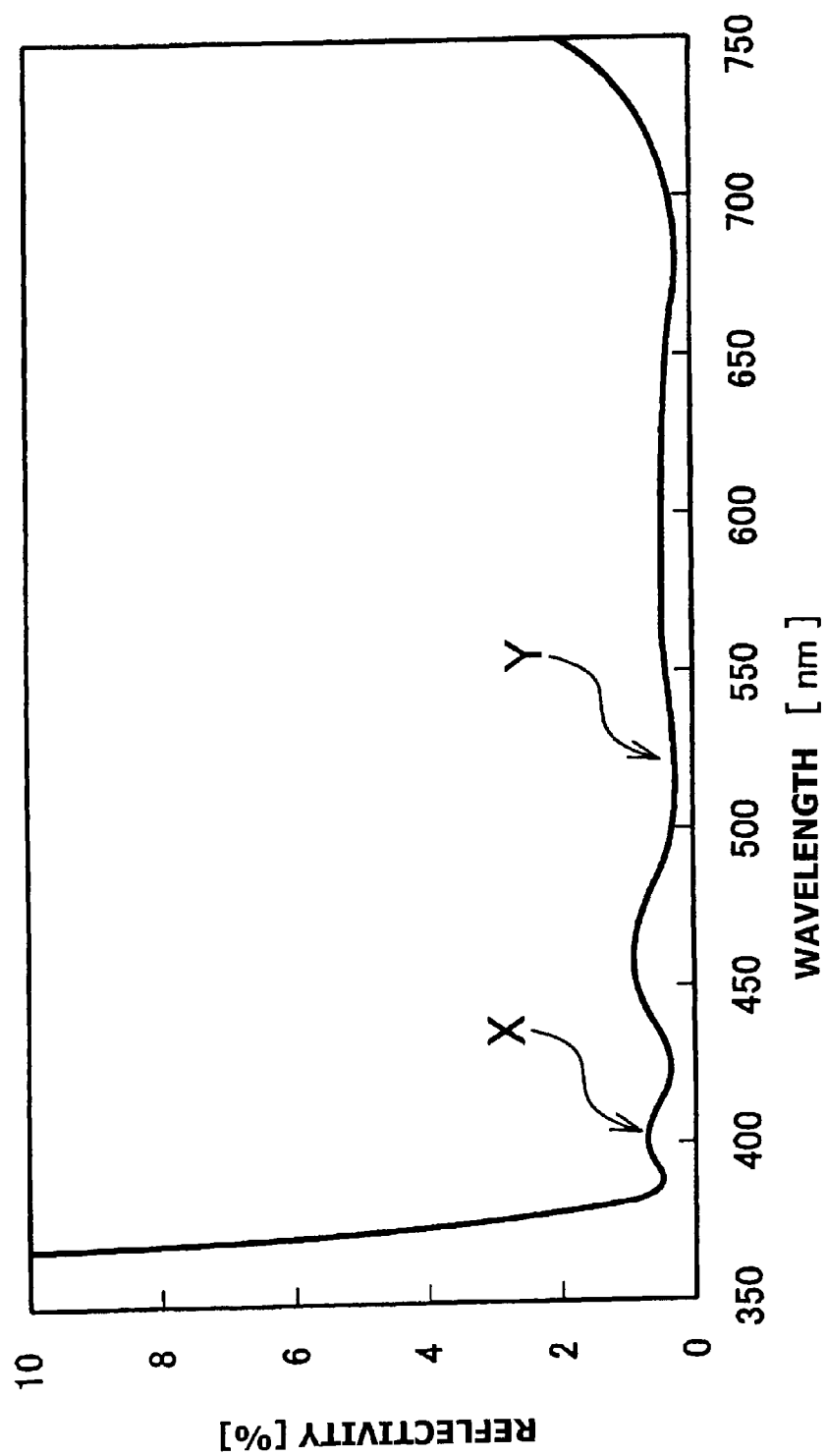
FIG. 6 is a graph showing the spectral reflection characteristics before and after the durability test of the antireflection film of FIG. 2.
Figure 7:
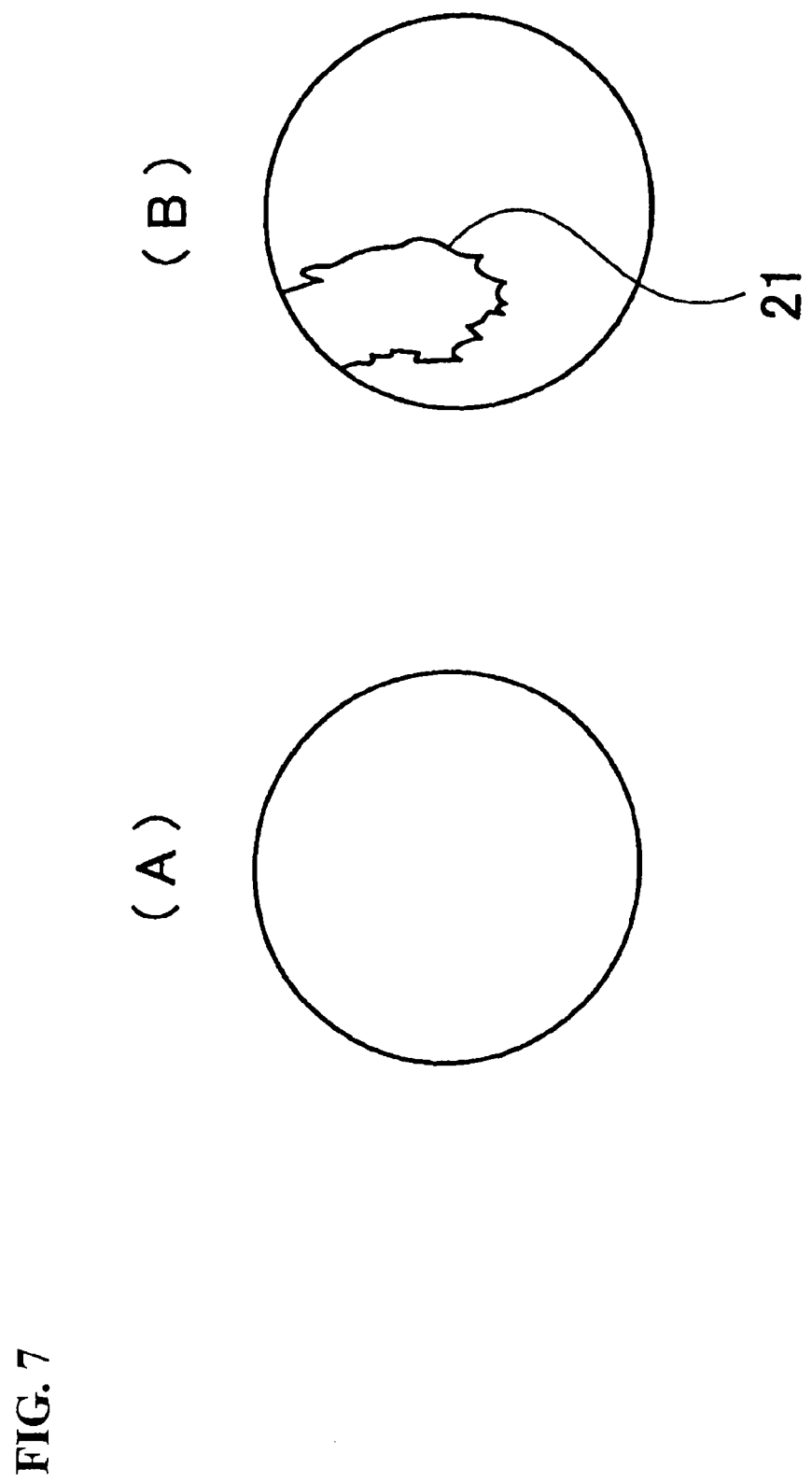
FIG. 7 is a diagram showing the condition of the film surface before and after the durability test of the antireflection film of comparative example 1.
Figure 8:
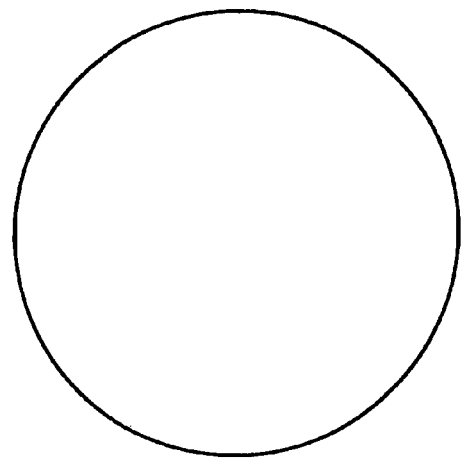
FIG. 8 is a diagram showing the condition of the film surface before and after the durability test of the antireflection film of comparative example 2.
Figure 8:
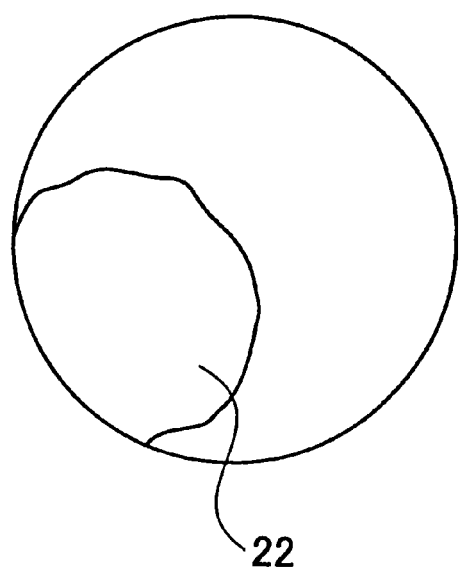

1 Oculus
2 Vitreous
3 Ocular fundus
10 Contact lens for vitreous surgery
11 Lens main body
13 Upper surface
14 Antireflection film
18 High refractive index layer
19 Low refractive index layer

The invention claimed is:

1. A contact lens for vitreous surgery used to observe an ocular fundus during vitreous surgery consisting of:
 only one lens for intraocular observation comprising a lens main body having a lens lower surface provided with a curved surface that matches a curvature of a cornea, and a lens upper surface for observing a vitreous or an ocular fundus, and which is held on the cornea by the lens lower surface and is used for observing inside an eye from the lens upper surface, and
 an antireflective film that is coated on at least a portion of the lens upper surface or the lens lower surface via an ion beam sputtering method, is durable to high-pressure steam for sterilization, and is made of a multilayered film in which a layer that contains silicon dioxide and a layer that contains tantalum pentoxide are alternately layered, and the topmost layer of the antireflective film is the layer that contains silicon dioxide,
 wherein a reflective coating is formed on neither the lens upper surface nor the lens lower surface.

2. The contact lens for vitreous surgery according to claim 1, wherein said antireflective film is coated on the lens upper surface.

3. The contact lens for vitreous surgery according to claim 1, wherein a target used in the ion beam sputtering method is a metal oxide.

4. The contact lens for vitreous surgery according to claim 1, wherein the lens for intraocular observation is formed of a material that is glass or transparent plastic.

5. The contact lens for vitreous surgery according to claim 1, wherein the lens upper surface is flat and sloped at a prescribed angle to a tangential plane of the lens lower surface.

6. The contact lens for vitreous surgery according to claim 5, wherein the angle is 5 to 70 degrees.

* * * * *